United States Patent
Kasdan

[11] Patent Number: 5,436,978
[45] Date of Patent: * Jul. 25, 1995

[54] METHOD AND AN APPARATUS FOR DIFFERENTIATING A SAMPLE OF BIOLOGICAL CELLS

[75] Inventor: Harvey L. Kasdan, Van Nuys, Calif.

[73] Assignee: International Remote Imaging Systems, Inc., Chatsworth, Calif.

[*] Notice: The portion of the term of this patent subsequent to Jun. 16, 2009 has been disclaimed.

[21] Appl. No.: 164,684

[22] Filed: Dec. 6, 1993

Related U.S. Application Data

[63] Continuation of Ser. No. 893,121, Jun. 3, 1992, abandoned, which is a continuation of Ser. No. 391,938, Aug. 10, 1989, Pat. No. 5,123,055.

[51] Int. Cl.⁶ ............................. G06K 9/00
[52] U.S. Cl. ......................... 382/133; 356/39
[58] Field of Search ............ 382/6, 8, 1, 17, 18, 382/51; 348/79, 80; 364/413.13; 356/39

[56] References Cited

U.S. PATENT DOCUMENTS

| | | | |
|---|---|---|---|
| 3,315,229 | 4/1967 | Smithline | 382/6 |
| 3,503,684 | 3/1970 | Preston, Jr. et al. | 356/39 |
| 3,705,383 | 12/1972 | Frayer | 382/6 |
| 3,822,095 | 7/1974 | Hirschfeld | 356/39 |
| 3,851,156 | 11/1974 | Green | 356/39 |
| 3,932,839 | 1/1976 | Stephens | 382/6 |
| 4,082,457 | 4/1978 | Kohno et al. | 356/39 |
| 4,125,828 | 11/1978 | Resnick et al. | 382/17 |
| 4,175,860 | 11/1979 | Bacus | 356/39 |
| 4,191,940 | 3/1980 | Polcyn et al. | 382/17 |
| 4,338,024 | 7/1982 | Bolz et al. | 382/6 |
| 4,426,731 | 1/1984 | Edlund et al. | 382/56 |
| 4,581,223 | 4/1986 | Kass | 424/3 |
| 4,731,663 | 3/1988 | Kovalchick et al. | 358/101 |
| 4,850,024 | 7/1989 | Motoike et al. | 356/39 |
| 5,086,476 | 2/1992 | Bacus | 356/39 |
| 5,123,055 | 6/1992 | Kasdan | 382/6 |
| 5,134,662 | 7/1992 | Bacus et al. | 382/6 |

*Primary Examiner*—Leo H. Boudreau
*Attorney, Agent, or Firm*—Limbach & Limbach; Alan S. Hodes

[57] ABSTRACT

A method for quickly and easily identifying the five basic components of leukocyte cells: basophils, eosinophils, neutrophils, monocytes and lymphocytes is disclosed. The method measures the size of each of the cells. Computation of the quantile feature of the cells and their color is then made. BA and EO cells are differentiated from LY and MO and NE cells using the present method. BA and EO cells can also be differentiated from LY, MO, and NE cells using methods of the prior art. Once BA and EO cells have been differentiated from the five leukocyte cells, LY cells can be differentiated from MO and NE cells based upon the size of the LY cells. The average color intensity of the LY cells determined is then used as the threshold to differentiate MO cells from NE cells.

10 Claims, 3 Drawing Sheets

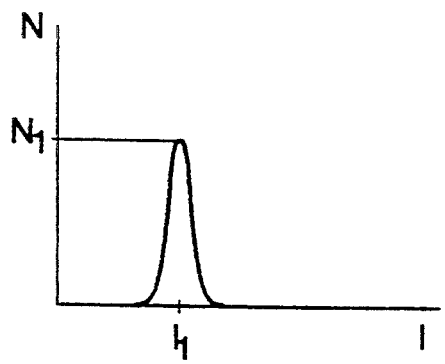
FIG. 2a
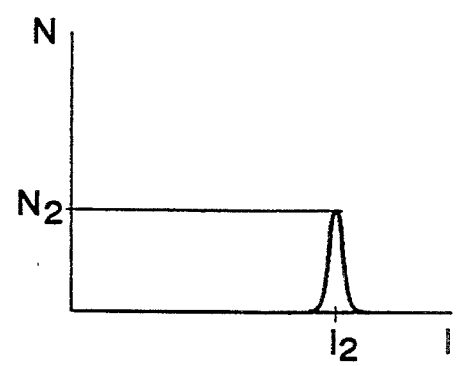
FIG. 2b
FIG. 2
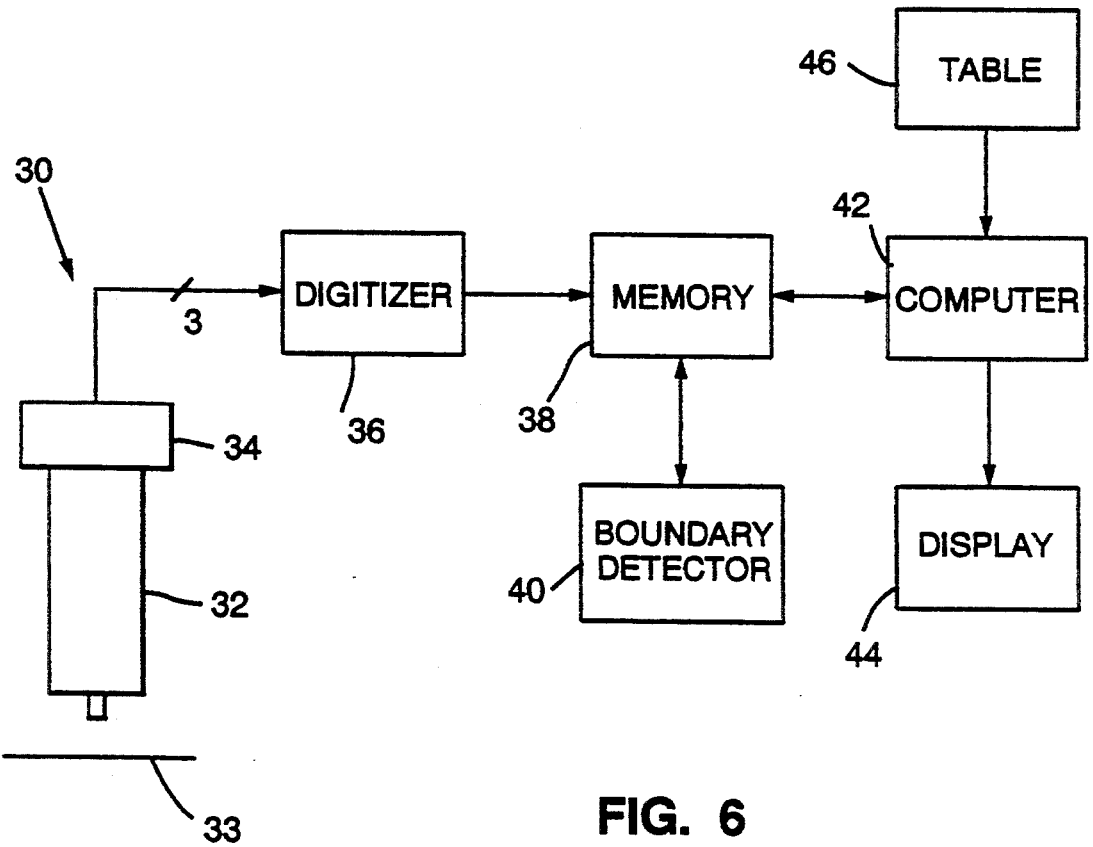
FIG. 6

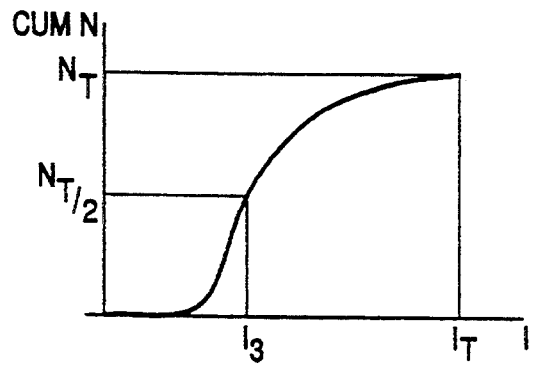
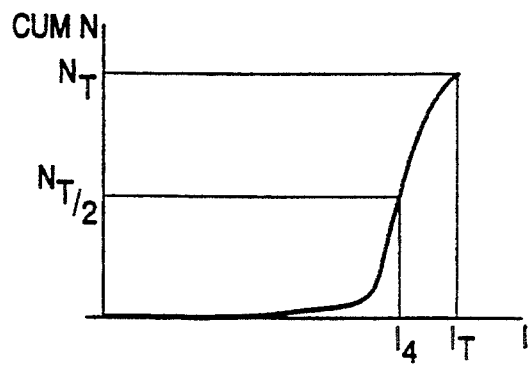
FIG. 3a  FIG. 3b
FIG. 3
| 50th QUANTILE | INTENSITY | OBJECT |
|---|---|---|
| | $I_a$ | xxx |
| | ⋮ | ⋮ |
| | $I_3$ | 12 |
| | ⋮ | ⋮ |
| | $I_4$ | 14 |
| | ⋮ | ⋮ |
| | $I_x$ | xxx |
FIG. 4

METHOD AND AN APPARATUS FOR DIFFERENTIATING A SAMPLE OF BIOLOGICAL CELLS

This is a continuation of application Ser. No. 07/893,121 filed on Jun. 3, 1992, now abandoned, which is a continuation of application Ser. No. 07/391,938, filed Aug. 10, 1989, now U.S. Pat. No. 5,123,055.

TECHNICAL DESCRIPTION

The present invention relates to a method and an apparatus to differentiate a sample of biological cells and more particularly to a method and an apparatus to differentiate lymphocyte cells from monocyte cells from neutrophil cells in a sample of blood cells containing a plurality of these cells.

BACKGROUND OF THE INVENTION

Methods and apparatuses for identifying an object are well-known in the art. The art of identifying biological samples is replete with various techniques for identifying the type of biological samples under examination. See, for example, U.S. Pat. No. 4,175,860. Formation of histograms of various parameters are also known. See for example U.S. Pat. No. 3,851,156.

Heretofore, one prior art, such as U.S. Pat. No. 4,175,860 teaches a method of differentiating white blood cells, based upon their size, color, shape, internal optical density, and other morphological parameters measured. Collectively these parameters require a considerable amount of computational resources to compute the parameters and to distinguish the various cells based upon the parameters. Thus far, to applicant's knowledge, there has not been a simple, efficient method of differentiating various different types of leukocyte cells in a fluid sample.

SUMMARY OF THE INVENTION

In the present invention, a method of differentiating certain types of leukocyte cells from one another is disclosed. The types of leukocyte cells are lymphocytes, monocytes, and neutrophils. In the method of the present invention the size of each of these cells is measured. The lymphocytes are then differentiated from the other cells based upon the size of each cell measured. Thereafter, the average color of the lymphocytes determined is measured. The monocyte and neutrophils are differentiated from one another based upon the comparison of the color of the monocytes and neutrophils to the average color of the lymphocyte cells determined.

BRIEF DESCRIPTION OF THE DRAWINGS

FIG. 2, comprising FIGS. 2a and 2b, is a graph showing a histogram of intensity of light versus the number of pixels in the boundary detected.

FIG. 3, comprising FIGS. 3a and 3b, is a graph showing a cumulative histogram of intensity of light versus the cumulative number of pixels in the boundary detected, and with the quantile feature determined for each object.

FIG. 4 is a table of pre-determined relationships or quantiles of various known objects.

FIG. 6 is a block diagram of an apparatus suitable for carrying out the method of the present invention.

DETAILED DESCRIPTION OF THE DRAWINGS

Figure 1:
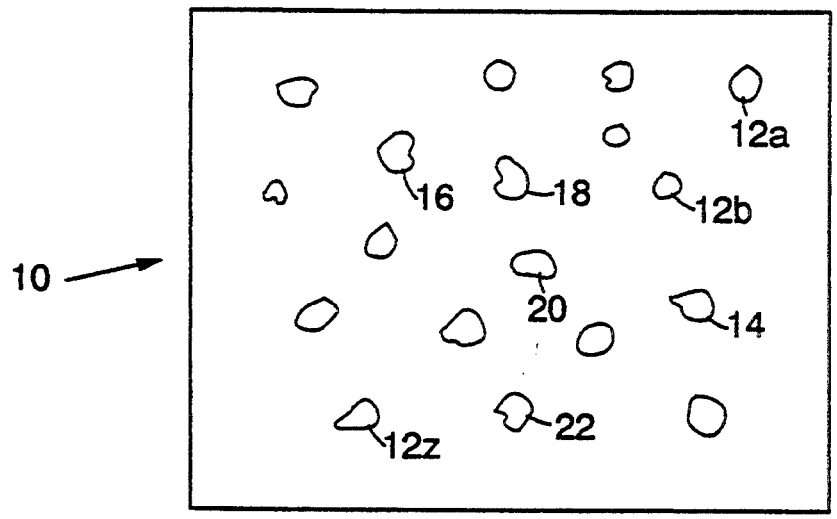
FIG. 1 is a schematic plan view of an image of a sample of fluid containing leukocyte cells to be differentiated in accordance with the method of the present invention.

Referring to FIG. 1 there is a shown a graphical plan view of an image 10 containing a plurality of different types of biological cells 12($a \ldots z$). The plurality of biological cells 12($a \ldots z$) includes a sample of leukocyte cells having lymphocyte (LY) cells 14, monocyte (MO) cells 16, neutrophil (NE) cells 18, eosinophil (EO) cells 20, and basophil (BA) cells 22. The method of the present invention differentiates the sample of leukocyte cells of LY, MO, NE, EO, and BA from one another.

In the method of the present invention, the sample of biological fluid is first subjected to a staining treatment by basic orange 21 dye. It is well known that basic orange 21 dye metachromatically stains leukocyte cells (i.e., LY, MO, NE, EO, and BA cells), so that these cells can be easily distinguished (see U.S. Pat. No. 4,581,223). The stained biological sample is placed in a biological imaging apparatus, such as that disclosed in U.S. Pat. No. 4,338,024.

The image 10 can be formed by using an electronic video camera, such as a CCD (the specific details of an apparatus suitable to carry out the method of the present invention will be discussed hereinafter). The image 10 is then filtered in accordance with the different color filters that can be used to distinguish the type of color of the object. Each of the different color images is segmented, to form a plurality of pixels. Each pixel is then digitized. The boundary of each of the objects 12($a \ldots z$) is determined. This can be done, for example, by the method disclosed in U.S. Pat. No. 4,538,299, which is incorporated herein by reference.

Once the boundary of each of the objects 12($a \ldots z$) is determined, one of the parameters of each pixel within the boundary is measured. One parameter can be the intensity of visible light. Thus, the intensity of visible light at each pixel, positioned within the boundary positions is measured. Thereafter, a histogram of intensity versus the number of pixels is formed.

Referring to FIG. 2, there is shown two histograms. The histogram of FIG. 2a corresponds to the object 12a whereas the histogram of FIG. 2b corresponds to the object 12b. Object 12a is assumed to have a substantially uniform bright intensity throughout the entire region within its boundary. Thus, the histogram, as shown in FIG. 2a, shows substantially $N_1$ pixels each having an intensity of $I_1$. In contrast, object 12b has a small area that has greater brightness intensity than the uniform intensity $I_1$ of object 12a. The histogram, as shown in FIG. 2b, shows that $N_2$ number of pixels in the bright spot have substantially an intensity value of $I_2$, with $N_1 > N_2$ and $I_2 > I_1$.

Once the histogram of each object 12a and 12b has been formed, a cumulative histogram is then developed. The cumulative histogram is formed by summing the number of pixels that has at least a certain intensity value. If $N = f(I)$, where N is the number of pixels having an intensity level I, then Cum $N = F(I)$ where Cum N is the cumulative number of pixels having an intensity level I, and where $F(I)=f(i)$ The cumulative histograms of the histograms shown in FIGS. 2a and 2b, are shown in FIG. 3. The particular parameter value, such as intensity of visible light, associated with a cumulative fraction of all pixels, is termed a quantile. Thus, from FIG. 3, the 50th quantile is $I_3$ for object 12a and $I_4$ for object 12b. It should be noted that unlike conventional percentile representations, which are even increments of discrete percents, quantile representations are not limited to discrete, even increments. Thus, an object may be identified by its ith, jth, or kth quantile, where i, j, and k do not necessarily occur in discrete, even increments.

Since the quantile relationship, shown in FIG. 3, associated with each objects 12a and 12b is different, the objects 12a and 12b can be distinguished from one another, based upon this developed quantile relationship. Alternatively, to uniquely identify a particular object, such as object 12b, the quantile relationship associated with the object 12b can be compared to a table of predetermined relationship of other known objects whose quantile relationships have been pre-determined. The table of pre-determined quantile relationships of other known objects can be based upon experimental results. The comparison of the quantile relationship to the table of pre-determined quantile relationships would then serve to identify uniquely the type of the object that is under examination.

For the purpose of distinguishing the objects 12a and 12b from one another or to identify an unknown object by comparing the quantile relationship, it is not necessary to compare each ordered pair of numbers (Q,I) (where Q is the quantile number and I is intensity associated therewith), to each other (in the case of two particles) or to a table (in the case of attempting to uniquely identify an object). One method is to compare the associated intensity value of the object under examination at a particular quantile number to the associated intensity value of another object at the same quantile number, or to a table of associated intensity values of identified objects at the same quantile number. Thus, as shown in FIG. 3, the 50th quantile for the object 12a has an intensity value of 13 and the same 50th quantile for the object 12b has the value 14. These intensity values can be compared to each other to distinguish one object from another. Alternatively, the 50th quantile of one of the objects can be compared to a table of intensity values of identified particles whose 50th quantile have been predetermined. See FIG. 4. By comparing the 50th quantile of the unknown object to the table, the unknown object can be identified.

Of course, if we are dealing with objects of biological particles having statistical variations in intensity, it may not be possible to determine precisely the intensity associated with a particular quantile for the same particle under all cases of examination. Thus, a table relationship may encompass a range of values of intensity for a particular quantile such that the object having that range of intensity values, can be uniquely identified. The range of values can be developed from representative samples identified from experimental results.

The foregoing example illustrates the method wherein the average intensity of the two objects 12a and 12b are indistinguishable. However, using the quantile method with the intensity of visible light and the cumulative histogram developed therefor, the objects can be distinguished from one another. Parameters, other than intensity of light can also be used to distinguish the particles. Thus, another parameter suitable for use is differentiating by color representation. Color can be represented by three primary colors of red, blue, and green. Alternatively, color can also be represented by hue, intensity, and saturation.

In one particular embodiment, the difference in color representation of the primary colors is used. The parameter of log(a)−log(b) may be employed, where a, and b are intensities of red and blue primary colors, respectively. Other possible combinations include: a being blue and b being green; or a being green and b being blue. The parameter of log(a)−log(b) is mathematically the same as log(a/b) or the ratio of the intensity of a pair of color values.

Referring back to FIG. 1, the cumulative histogram of intensity values within the boundary for each color of each of the leukocyte cells is also determined. In addition, the cumulative histogram of the intensity values outside the boundary for each color is also determined. The cumulative histogram of intensity values is calculated as previously discussed.

The normalized interior pixel values for each color can be computed using:

$p_n = (p-p_p)*200/q_a$ $p_o$ = dark noise value for one of said different colors
$q_a$ = a particular quantile value for the pixels exterior to all the cells.

Figure 5:
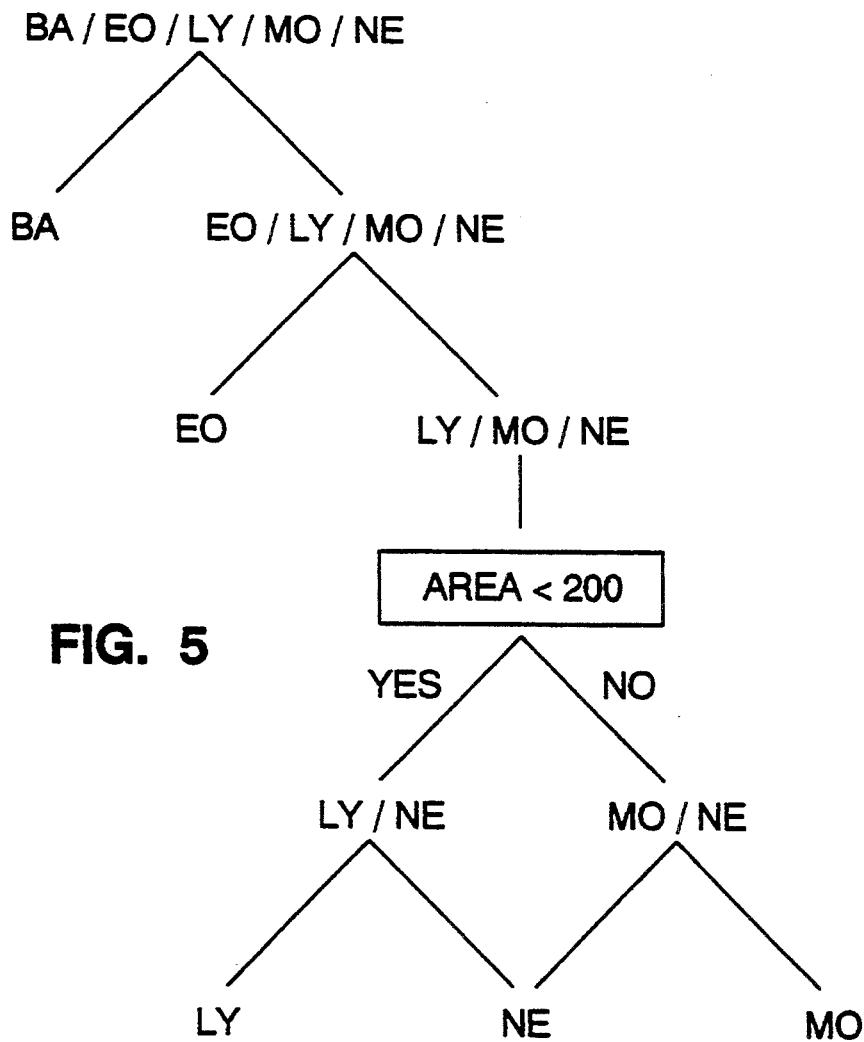
FIG. 5 is a schematic diagram of a decision tree which is used in the method of the present invention to differentiate lymphocyte cells, monocyte cells, neutrophil cells, eosinophil cells, and basophil cells from one another.

Thereafter, the quantiles, such as the 50th quantile, for each individual color using the normalized interior pixels is calculated. The various quantiles are paired with each of the three primary colors. Each of the colored pairs for the various quantiles can be computed in accordance with the following formula:

$bmg = \log(bp_n) - \log(gp_n) = \log(bp_n/gp_n)$ $gmr = \log(gp_n) - \log(rp_n) = \log(gp_n/rp_n)$ $rmb = \log(rp_n) - \log(bp_n) = \log(rp_n/bp_n)$ where
 b = blue, g = green, r = red
 $bp_n$ = normalized blue interior pixel
 $gp_n$ = normalized green interior pixel
 $rp_n$ = normalized red interior pixel Finally, a tree decision rule, as set forth in FIG. 5, can be used to identify the various leukocyte cells, such as BA, EO, LY, MO, and NE.

Referring to FIG. 5, there is shown the tree decision rule above. In accordance with the method of the present invention, all of the cells stained by basic orange 21 are the leukocyte cells of interest. To differentiate BA cells from all of the leukocyte cells, the following decision rule is implemented:

if $(0.875*qbi0 - qgi0) > 0$ for a cell then said cell is BA cell.
where:
 qbi0—is the zeroth quantile of the blue channel intensity or minimum blue intensity
 qgi0—is the zeroth quantile of the green channel intensity or minimum green intensity Once the BA cells have been differentiated, the remaining cells, EO, LY, MO, and NE form a subpopulation upon which the following decision rule can be used to differentiate the EO cells from the rest of the cells:

if d0t>LY(AVE(d0t))*4.345+190.0 then said cell is EO cells, d0t=0.093*gbi0+70−qgi0

LY(AVG(d0t))—is the average value of d0t computed for cells less than 200 pixels in area. For cells less then 200 pixel in area, 95+% of which will be LY cells. Thus, the operand LY is used to denote that the term is the average value of the d0t computed for LY cells.

Once the EO cells have been differentiated, the remaining cells comprise of LY, MO, and NE. This subpopulation is further differentiated in the following manner.

The size of a cell measured is compared to 200 pixels, and is then further subdivided into a first group of cells (LY & NE) whose size is less than 200 pixels, and into a second group of cells (MO & NE) whose size is greater than or equal to 200 pixels.

For the first group of cells (LY & NE), if d1t<1600, then those cells that satisfy this criterion are LY cells and all others are NE cells where:

d1t−2.817*(sdrmb−2125)−qbmg2 sdrmb—is the standard deviation of the term rmb (as previously defined).

qbmg2—is the second quantile of the term bmg

Once the LY cells are differentiated from NE cells, the average color of the LY cells differentiated is then determined.

The color of the average intensity of the LY cells determined is then used as the threshold to differentiate MO cells from NE cells. In the event a cell has its color intensity greater than the average color of the LY cells determined, then it is an NE cell. Those cells having color intensity less than the average color of the LY cells are determined to be MO cells. This is accomplished in accordance with the following:

if d1t<LY(AVG(qbi0))*(−95.47)+9062, where

LY(AVG(qbi0))—is the average value of qbi0 computed for cells less than 200 pixels in area. For cells less than 200 pixel in area, 95+% of which will be LY cells. Thus, the operand LY is used to denote that the term is the average value of the d0t computed for LY cells.

An apparatus 30 suitable for carrying out the method of the present invention is shown in FIG. 6. The apparatus 30 comprises a microscope 32, which is focused on an examination area 33. The examination area can be a microscopic slide or a flow cell such as that disclosed in U.S. Pat. No. 4,338,024. A camera 34 is attached to the microscope 32 and is adapted to image a portion of a suspension having a particle therein. The camera 34 is preferably of a raster scan type and may be a CCD camera model TC1160BD manufactured by RCA. The camera 34 can form an electrical image of the field of view as seen through the microscope 32. Further, the camera 34 segments the image into a plurality of pixels, with an electrical signal corresponding to each pixel of the image. The camera 34 also outputs a plurality of signals (3) one for each of the colors (Red, Blue, and Green).

Each of the signals from the camera 34 is supplied to a digitizer 36, which digitizes the image intensity of each pixel into an electrical signal representing the grey scale value. Preferably, the pixel is digitized into a gray scale value between 0 and 256.

From the digitizer, the digitized gray scale value is supplied to a memory 38, where the values are stored. The memory 36 can be a RAM. A boundary detector 40, such as that disclosed in U.S. Pat. No. 4,538,299 operates on the image in the memory 38 and detects the boundary of the image detected. The result is also stored in the memory 38.

From the memory 38, a computer 42 operates on the image and measures a parameter, such as intensity of light, of each pixel within the boundary detected. The computer 42 then establishes a histogram of those measurements. From the histogram developed, the computer 42 forms a cumulative histogram. Then, the computer 42 executes the method of the present invention in accordance with the decision tree discussed hereinabove. A program to be executed by the computer 42 is attached as APPENDIX A. The program is a listing of the computed fields in a Reflex database program (a program available from Borlund Software Company).

As can be seen from the foregoing, the method of the present invention allows identification of five basic leukocyte cells using simple features of size and color without requiring detailed analysis of the morphology of the cells. Thus, computation time is greatly decreased, and cell classification can be determined more rapidly. This, of course, results in greater throughput thereby increasing the capability of a medical diagnostic instrument to process a greater number of biological samples.

```
d0t  =(13 /140)   qbi0 + 70 − qgi0
d1t  =(5000 / (2125 − 350))   (sdrmb − 2125) − qbmg2
d2t  =0.875   qbi0 − qgi0
DL   =@IF(d2t > 0, 0, 8)
DL1  =@IF(d0t > Td0t, 0, 4)
DL11 =@IF(carea < 200, 0, 2)
DL110=@IF(d1t < 1100, 0, 1)
DL111=@IF(d1t < Td1t, 0, 1)
LYAVGd0t = −46.93
LYAV6d1t = −1108
LYAVGqbi0 =@CASE(set = "M2201", 97.39, set = "M2202",
 91.75, set = "M2301", 97, set = "M2401", 106.93, set = "M2501", 112.92,
 set = "M2502", 99.29, set = "M2901", 98.13, set = "M3001", 110.19)
MD =@CASE(DL = 0, "BA", DL + DL1 = 8, "ED",
 DL + DL1 + DL11 + DL110 = 12, "LY",
 DL + DL1 + DL11 + DL110 = 13, "NE", DL +
 DL1 + DL11 + DL111 = 14, "MO",
 DL + DL1 + DL11 + DL111 = 15, "NE", @TRUE, "ND")
set =@CASE(file("MAR22401.101","M2201",
file<"MAR22402.101","M2202",file<"MAR23401.101","M2301",file<"MAR24401.101",
"M2401",file<"MAR25401.101","M2501",file<"MAR25402.101",=M2502",
file<"MAR29401.101","M2901",file<"MAR30401.101","M3001")
Td0t =LYAVGd0t   4.344748076 + 190.93346634
```

Td1t =LYAYGqbi0 (−95.474172397) + 9062.41

What is claimed is:

1. A method of differentiating a sample of a plurality of different types of biological cells from one another in a field of view, said method comprising the steps of:
   forming an image of said sample;
   segmenting said image to form a plurality of pixels;
   determining the boundary of each cell in said field of view;
   measuring the intensity values of each individual pixel within the boundary of each cell for a plurality of different colors;
   computing one or more ratios of the intensity values of the different colors measured for each pixel; and
   identifying one or more of said different types of cells based upon said ratio computed.

2. The method of claim 1 wherein said biological cells are White Blood Cells (WBC).

3. The method of claim 2 wherein said WBC cells comprise: Lymphocyte (LY) cells, monocyte (MO) cells, and neutrophil (NE) cells.

4. The method of claim 1 wherein said plurality of different colors are: red, blue and green.

5. The method of claim 1 wherein said computing step computes a plurality of ratios.

6. The method of claim 5 further comprising the step of:
   measuring the intensity values of the pixels outside the boundary of each cell for said same plurality of different colors; and
   computing the normalized intensity values of the pixels within the boundary of each cell, prior to computing the ratio therefor.

7. The method of claim 5 further comprising the step of:
   measuring the size of each cell;
   differentiating one type of cell from other types of cells based upon the size of each cell measured;
   after the step to determine the boundary of each cell.

8. The method of claim 7 further comprising the step of:
   measuring the intensity values of the pixels outside the boundary of each cell for said same plurality of different colors; and
   computing the normalized intensity values of the pixels within the boundary of each cell, prior to computing the ratio therefor.

9. The method of claim 8 wherein said plurality of different colors are: red, blue and green.

10. The method of claim 1 further comprising the step of:
    computing a plurality of quantiles of the ratios computed; and
    identifying one or more of said different types of cells based upon said quantiles of ratios computed.

* * * * *